Figure 1:
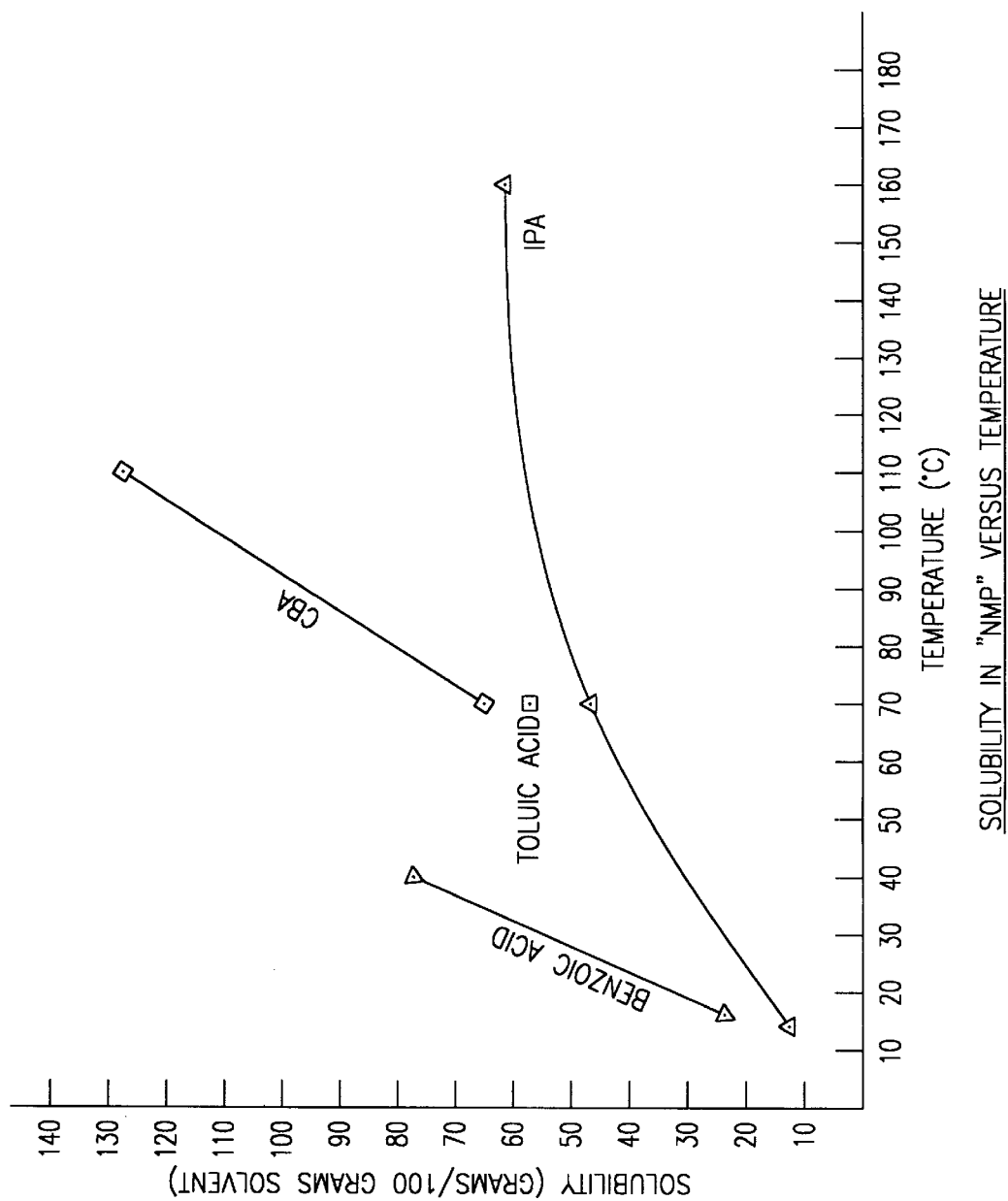

United States Patent [19]
Lee et al.

[11] Patent Number: 6,140,534
[45] Date of Patent: Oct. 31, 2000

[54] METHOD FOR PURIFYING ISOPHTHALIC ACID PREPARED FROM METAXYLENE

[75] Inventors: Fu-Ming Lee; Wiston Lamshing, both of Katy, Tex.; Randi Wright Wytcherley, Belgrade, Mont.

[73] Assignee: HFM International, Inc., Houston, Tex.

[21] Appl. No.: 09/229,789

[22] Filed: Jan. 13, 1999

Related U.S. Application Data

[63] Continuation-in-part of application No. 08/477,898, Jun. 7, 1995, Pat. No. 5,767,311.
[60] Provisional application No. 60/084,426, May 6, 1998.
[51] Int. Cl.⁷ .......................... C07C 51/42; C07C 51/43
[52] U.S. Cl. .......................... 562/485; 562/486; 562/409; 562/414
[58] Field of Search .................................. 562/409, 414, 562/494, 485, 486

[56] References Cited

U.S. PATENT DOCUMENTS

| | | | |
|---|---|---|---|
| 2,949,483 | 8/1960 | Ham | 260/516 |
| 5,110,984 | 5/1992 | Janulis | 562/487 |

FOREIGN PATENT DOCUMENTS

| | | |
|---|---|---|
| 0 818 434 | 1/1998 | European Pat. Off. . |
| 96/40612 | 12/1996 | WIPO . |

*Primary Examiner*—Johann Richter
*Assistant Examiner*—Rosalynd Keys
*Attorney, Agent, or Firm*—Jenkens & Gilchrist, A Professional Corporation

[57] ABSTRACT

Disclosed is a method for preparing isophthalic acid from metaxylene and especially for purifying crude isophthalic acid (IPA) produced in the course of such method, or otherwise, from a liquid dispersion thereof also containing impurities selected from unreacted starting materials, solvents, products of side reactions and/or other undesired materials. The purifying portion of the method comprises the step of: (1) filtering the dispersion to form a crude IPA filter cake; (2) dissolving the filter cake in a selective crystallization solvent at an elevated temperature to form a solution; (3) crystallizing purified IPA from the solution in the crystallization solvent by reducing the temperature, or pressure, or both of the solution; (4) separating the crystallized purified IPA from the solution; and (5) re-dissolving or soaking the washed purified IPA cake at elevated temperature, to remove the final traces of the crystallization solvent and obtain the desirable particle sizes and shape. Preferably, the selective crystallization solvent is N-methyl pyrrolidone.

25 Claims, 1 Drawing Sheet

METHOD FOR PURIFYING ISOPHTHALIC ACID PREPARED FROM METAXYLENE

This application is a Continuation-in-Part of U.S. application Ser. No. 08/477,898, filed Jun. 7, 1995, entitled "Method and Apparatus for Preparing Purified Terephthalic Acid," issued Jun. 16, 1998 as U.S. Pat. No. 5,767,311.

This is a conventional application based on and claiming priority from provisional patent application Ser. No. 60/084,426, filed May 6, 1998, entitled Method and Apparatus for Preparing Isophthalic Acid From Metaxylene, the disclosure of which is incorporated herein by reference for all purposes.

The present invention relates to a method and apparatus for preparing isophthalic acid (IPA) from metaxylene. It also relates to methods and apparatus for purifying the oxidation reactor effluent containing the mixture of isophthalic acid as well as minor amounts of 3-carboxybenzaldehyde (3-CBA), m-toluic acid, and other minor impurities, to produce a purified isophthalic acid in an integrated process. Isophthalic acid is useful in copolymerization processes for the production of fibers, films, plastic bottles, and polyester resin structures, often reinforced by other materials such as glass fiber.

SUMMARY OF THE INVENTION

In accordance with the present invention there is provided a method and apparatus for producing purified isophthalic acid from metaxylene in an integrated process. In one aspect, the method includes the production of crude isophthalic acid by the oxidation of the metaxylene. The oxidation step produces not only isophthalic acid, but also, by incomplete oxidation, produces 3-CBA, m-toluic acid and other trace amounts of acid and aldehyde isomers. The product produced in the oxidation step is a liquid dispersion containing unreacted starting materials, solvents, if any have been used, the products of side reactions, particularly those just mentioned, and other materials which are not desired in the sought-for purified isophthalic acid.

The reactor effluent is fed to a series of crystallizers to allow the isophthalic acid crystals to grow by evaporating the reaction solvent, preferably acetic acid, through pressure reductions. The slurry from the last crystallizer is filtered and washed. The filtered crystals are then dried to remove the solvent to a level of less than 0.25% in the crude IPA crystals. The mother liquor from the filtration is fed to the solvent dehydration unit to recover the solvent (acetic acid) from water for recycling to the oxidizer.

In further accordance with the invention, the crude IPA from the dryer of the oxidation section is re-dissolved in a selective crystallization solvent and then crystallized out of the selective crystallization solvent in one or, preferably, two crystallization stages. It is preferred that the dissolution temperature be between about 50 and about 200° C. Provision is made to separate out the crystallized and progressively more purified IPA from the solvent (with or without co-solvents) of the invention. The filter cake of purified IPA ultimately obtained is washed and soaked with other solvents of the invention to remove color and the final traces of the selective crystallization solvent from the IPA product.

The invention also contemplates steps to reclaim and recycle the solvents of the invention at each stage of crystallization and washing, and final soaking. Steps are also taken to closely control the delivery of any objectionable materials to the environment.

In an important aspect, the present invention is based on discoveries relating to solvents which are effective to bring about the purification of crude IPA through crystallization and separation steps. These discoveries may be summarized in several ways as follows.

The selective crystallization solvents useful in the practice of the present invention include those in which (a) the impurities desired to be separated from IPA are relatively more soluble in the solvent than is IPA at substantially every temperature within the desired range of temperatures at which the solvent containing IPA is to be handled, and (b) IPA is more soluble at an elevated temperature and less soluble at a lower or reduced temperature. It is to be understood that the term "selective crystallization solvent" is intended to mean solvents useful in the selective crystallization of IPA as described above and as described in greater detail below and as shown in FIG. 1.

In accordance with the invention, the primary preferred selective crystallization solvent is N-methyl pyrrolidone (NMP), for the several reasons discussed below, and for its superior performance. It is non-aqueous, thermally stable, non-toxic (environmentally safe), non-corrosive, and commercially available. As shown in FIG. 1, its solubility versus temperature curve indicates that IPA can be dissolved in NMP at elevated temperatures, and precipitated or crystallization from NMP at lower temperatures. The major impurities such as CBA (indicated by 4-CBA) and toluic acid (indicated by p-toluic acid) have much higher solubility in NMP than IPA at all temperatures. Therefore, by lowering the temperature, only IPA tends to crystallize or precipitate from the solution to form purified IPA crystals.

Although NMP is the most preferred selective crystallization solvent, it is to be understood that, in accordance with the present invention, other preferred selective crystallization solvents for purification of crude IPA can be selected from various polar organic solvents including, but not intended to be limited to, N,N-dimethyl acetamide, N,N-dimethyl formamide, N-formyl piperidine, N-alkyl-2-pyrrolidone (such as N-ethyl pyrrolidone), N-mercatoalkyl-2-pyrrolidone (such as N-mercaptoethyl-2-pyrrolidone), N-alkyl-2-thiopyrrolidone (such as N-methyl-2-thiopyrrolidone), N-hydroxyalkyl-2-pyrrolidone (such as N-hydroxyethyl-2-pyrrolidone), the morpholines (such as morpholine, and N-formyl morpholine), the carbitols, $C_1$ to $C_{12}$ alcohols, the ethers, the amines, the amides, the esters, and mixtures thereof.

In order to remove the residual solvent trapped in the crystals of the final IPA product, the washed IPA crystals are preferably fed to a high temperature soaker where water is used to partially or completely dissolve the IPA crystals. When the IPA crystals are again precipitated or otherwise separated from the soaking water, the residual solvent stays behind in the water. In addition to water (which is preferred), other solvents may be utilized to displace the selective crystallization solvent including methanol, methyl ethyl ketone, and acetone. It is preferred to soak or re-dissolve the purified IPA cake in water at temperatures between about 150 and about 280° C. to remove the final trace amount of crystallization solvent and to obtain the desirable IPA particle size and shape.

The following examples illustrate the principles and features of the invention.

EXAMPLE 1

Purifying Crude IPA by Cooling Crystallization 350 g of NMP (solvent), 207.9 g of isophthalic acid (IPA), 2.1 g of 3-CBA, and 0.21 g of m-toluic acid were added to a crystallizer equipped with a heating mantle, thermocouple, condenser, and overhead stirrer. The mixture was heated to 125° C. until the solids were totally dissolved under agitation and the solution was kept at 125° C. for about one hour before cooling started. The solution was slowly cooled to 40° C. in two to four hours to allow the IPA crystals to grow. The slurry was then removed from the crystallizer and filtered at 45 to 50° C. The filtered cake (210 g) was rinsed with 630 g of NMP solution saturated with IPA (the solution contained 25 g IPA per 100 g NMP) to remove the trapped mother liquor from the cake. Clean NMP may be used for rinsing, but it is preferred to utilize NMP saturated with IPA to minimize losses due to cake washing. One half of the rinsed cake was rinsed again at room temperature with an equal amount of saturated NMP solution (11 g IPA per 100 g NMP). In addition to clean or saturated NMP, other solvents may be used for washing, including p-xylene, methanol, acetone, and methyl ethyl ketone.

The rinsed crystals were dried and analyzed by gas chromatography for composition and the results are summarized below:

| Run No. | Feed Composition | | | Product Crystal Composition | |
|---|---|---|---|---|---|
| | % 3-CBA | % m-toluic | % solvent | % 3-CBA | % m-toluic |
| 1a | 1.00 | 0.10 | 58.3 | 0.0139 | <2 ppm |
| 1b | 1.00 | 0.10 | 58.5 | 0.0039 | <2 ppm |
| 2a | 1.00 | 0.10 | 58.5 | 0.0038 | <2 ppm |
| 2b | 1.00 | 0.10 | 58.8 | 0.0027 | <2 ppm |

Notes: (a) Run 2 was duplicated run of Run 1.
(b) "a" was the analysis of crystals rinsed with saturated NMP at 3:1 ratio at 40° C.; and "b" was the analysis of crystal from "a" with one additional rinse at room temperature at 1:1 ratio.

In Run 1, with one-stage crystallization, 3-CBA was reduced substantially from 1.00% to 39 ppm and m-toluic acid was reduced from 0.10% to less than 2 ppm (experimental detection limit). In Run 2, with one-stage crystallization, 3-CBA reduced from 1.00% to 27 ppm and m-toluic acid reduced from 0.10% to less than 2 ppm. Therefore, it was concluded that only one-stage crystallization using NMP as the solvent is required to purify the crude IPA (containing up to 1% 3-CBA and 0.1% m-toluic acid) to an IPA product with less than 40 ppm 3-CBA and 2 ppm m-toluic acid.

It is preferred that the temperature of the solution be reduced to from between about 5 and about 100° C., and especially preferred that it be reduced to from between about 10 and about 45° C.

EXAMPLE 2

Separation of IPA from 4-CBA and p-Toluic Acid

The experimental procedure in EXAMPLE 1 was repeated with 4-CBA replacing 3-CBA and p-toluic acid replacing m-toluic acid. This experiment was conducted to make sure the small amount of other impurity isomers in crude IPA, such as 4-CBA and p-toluic acid, do not cause any problem in the process of this invention for producing purified IPA. The gas chromatographic analysis of the purified IPA is given below. Again, one-stage crystallization with NMP as the solvent was used for the purification.

| Run No. | Feed Composition | | Product Crystal Composition | |
|---|---|---|---|---|
| | % 4-CBA | % p-toluic | % 4-CBA | % p-toluic |
| 1 | 1.00 | 0.00 | 0.0015 | 0.0000 |
| 2 | 0.99 | 0.10 | 0.0035 | 0.0007 |
| 3 | 1.00 | 0.10 | 0.0029 | 0.0008 |
| 4 | 1.00 | 0.10 | 0.0064 | 0.0009 |
| 5 | 1.00 | 0.10 | 0.0039 | 0.0015 |

Note: All product crystals were rinsed with saturated NMP at 40° C. at 3:1 solvent to solid ratio.

Again, the product analysis has shown that the 4-CBA (1.00%) and p-toluic acid (0.10%) can be effectively reduced to ppm level through one-stage crystallization using NMP as the solvent.

What is claimed is:

1. A method for purifying crude isophthalic acid (IPA) from a liquid dispersion thereof also containing impurities selected from unreacted starting materials, solvent, products of side reactions and/or other undesired materials comprising:
    filtering said dispersion to form a crude IPA filter cake;
    dissolving said filter cake in a selective crystallization solvent at an elevated temperature of from between about 50 and about 200° C. to form a solution;
    crystallizing purified IPA from said solution in said crystallization solvent by reducing the temperature or reducing the pressure sufficient to flash evaporate solvent from said IPA of said solution;
    separating said crystallized purified IPA from said solution;
    washing the purified IPA cake with a clean or IPA saturated solvent to displace the mother liquor and color bodies; and
    re-dissolving or soaking the washed IPA cake in water at elevated temperatures.

2. A method in accordance with claim 1 in which said dispersion contains 3-carboxybenzaldehyde (3-CBA) and m-toluic acid.

3. A method in accordance with claim 1 in which the temperature of said solution is reduced to from between about 5 and about 100° C.

4. A method in accordance with claim 3 in which the temperature of said solution is reduced to from between about 10 and about 45° C.

5. A method in accordance with claim 1 wherein said selective crystallization solvent is N-methyl pyrrolidone (NMP).

6. A method in accordance with claim 1 wherein said selective crystallization solvent is selected from the group consisting of N,N-dimethyl acetamide, N,N-dimethyl formamide, N-formyl piperidine, N-alkyl-2-pyrrolidone, N-ethyl pyrrolidone, N-mercaptoalkyl-2-pyrrolidone, N-mercaptoethyl-2-pyrrolidone, N-alkyl-2-thiopyrrolidone, N-methyl-2-thiopyrrolidone, N-hydroxyalkyl-2-pyrrolidone, N-hydroxyethyl-2-pyrrolidone, the morpholmes, N-formyl morpholine, the carbitols, $C_1$ to $C_{12}$ alcohols, the ethers, the amines, the amides, and the esters, and mixtures thereof.

7. A method in accordance with claim 1 wherein the washing step of said filter cake utilizes a wash solvent selected from the group consisting of clean or IPA saturated NMP, p-xylene, methanol, acetone, and methyl ethyl ketone.

8. A method in accordance with claim 7 wherein said wash solvent is clean or IPA saturated NMP.

9. A method for purifying crude isophthalic acid (IPA) from a liquid dispersion thereof also containing impurities selected from unreacted starting materials, solvent, products of side reactions and/or other undesired materials comprising:

filtering said dispersion to form a crude IPA filter cake;

dissolving said filter cake in a selective crystallization solvent at an elevated temperature of from between about 50 and about 200° C. to form a solution;

crystallizing purified IPA from said solution in said crystallization solvent by reducing the temperature or reducing the pressure sufficient to flash evaporate solvent from said IPA of said solution;

separating said crystallized purified IPA from said solution;

washing the purified IPA cake with a clean or IPA saturated solvent to displace the mother liquor and color bodies;

re-dissolving or soaking the washed IPA cake in water at elevated temperatures; and displacing said selective crystallization solvent subsequent to the step of crystallizing with a displacement solvent selected from the group consisting of water, methanol, methyl ethyl ketone, and acetone.

10. A method in accordance with claim 9 wherein said displacement solvent is water.

11. A method in accordance with claim 1 wherein said re-dissolving or soaking the purified IPA cake in water is carried out at temperatures between about 180 to about 280° C., to remove the final trace amount of crystallization solvent and to obtain the desirable IPA particle sizes and shape.

12. A method for preparing isophthalic acid (IPA) comprising:

oxidizing metaxylene in a reaction solvent to produce a liquid dispersion thereof in said reaction solvent, said dispersion also containing impurities selected from unreacted starting materials, entrapped reaction solvent, products of side reactions, and/or other undesired materials: filtering said dispersion to form a crude IPA filter cake;

dissolving said filter cake in a selective crystallization solvent at an elevated temperature of from between about 50 and about 200° C. to form a solution;

crystallizing purified IPA from said solution in said crystallization solvent by reducing the temperature or reducing the pressure sufficient to flash evaporate solvent from said IPA of said solution;

separating said crystallized purified IPA from said solution;

washing the purified IPA cake with a clean or IPA saturated solvent to displace the mother liquor and color bodies; and re-dissolving or soaking the washed IPA cake in water at elevated temperatures.

13. A method in accordance with claim 12 in which the solvent that said metaxylene is oxidized in is acetic acid.

14. A method in accordance with claim 12 in which said dispersion contains 3-carboxybenzaldehyde (3-CBA) and m-toluic acid.

15. A method in accordance with claim 12 in which the temperature of said solution is reduced to from between about 5 and about 100° C.

16. A method in accordance with claim 15 in which the temperature of said solution is reduced to from between about 10 and about 45° C.

17. A method in accordance with claim 12 wherein said selective crystallization solvent is N-methyl pyrrolidone (NMP).

18. A method in accordance with claim 12 wherein said selective crystallization solvent is selected from the group consisting of N,N-dimethyl acetamide, N,N-dimethyl formamide, N-formyl piperidine, N-alkyl-2-pyrrolidone, N-ethyl pyrrolidone, N-mercaptoalkyl-2-pyrrolidone, N-mercaptoethyl-2-pyrrolidone, N-alkyl-2-thiopyrrolidone, N-methyl-2-thiopyrrolidone, N-hydroxyalkyl-2-pyrrolidone, N-hydroxyethyl-2-pyrrolidone, the morpholines, N-formyl morpholine, the carbitols, $C_1$ to $C_{12}$ alcohols, the ethers, the amines, the amides, and the esters, and mixtures thereof.

19. A method in accordance with claim 12 wherein the washing step of said filter cake utilizes a wash solvent selected from the group consisting of clean or IPA saturated NMP, p-xylene, methanol, acetone, and methyl ethyl ketone.

20. A method in accordance with claim 19 wherein said wash solvent is clean or IPA saturated NMP.

21. A method for preparing isophthalic acid (IPA) comprising:

oxidizing metaxylene in a reaction solvent to produce a liquid dispersion thereof in said reaction solvent, said dispersion also containing impurities selected from unreacted starting materials entrapped reaction solvent products of side reactions and/or other undesired materials:

filtering said dispersion to form a crude IPA filter cake;

dissolving said filter cake in a selective crystallization solvent at an elevated temperature of from between about 50 and about 200° C. to form a solution;

crystallizing purified IPA from said solution in said crystallization solvent by reducing the temperature or reducing the pressure sufficient to flash evaporate solvent from said IPA of said solution;

separating said crystallized purified IPA from said solution;

washing the purified IPA cake with a clean or IPA saturated solvent to displace the mother liquor and color bodies;

re-dissolving or soaking the washed IPA cake in water at elevated temperatures; and displacing said selective crystallization solvent subsequent to the step of crystallizing with a displacement solvent selected from the group consisting of water, methanol, methyl ethyl ketone, and acetone.

22. A method in accordance with claim 21 wherein said displacement solvent is water.

23. A method in accordance with claim 12 wherein said re-dissolving or soaking the purified IPA cake in water is carried out at temperatures between about 180 to about 280° C., to remove the final trace amount of crystallization solvent and to obtain the desirable IPA particle sizes and shape.

24. A method in accordance with claim 12 in which said liquid dispersion is formed by feeding effluent from said oxidizing step to a series of crystallizers to allow isophthalic acid crystals to grow by evaporating the reaction solvent and filtering said crystals to form said crude IPA filter cake, and drying said crude IPA filter cake to remove reaction solvent.

25. A method in accordance with claim 24 in which mother liquor from said filtering step is dehydrated to recover solvent and recycle it to said oxidizing step.

* * * * *

UNITED STATES PATENT AND TRADEMARK OFFICE
CERTIFICATE OF CORRECTION

PATENT NO : 6,140,534
DATED : October 31, 2000
INVENTOR(S) : Fu-Ming Lee, et al.

It is certified that error appears in the above-identified patent and that said Letters Patent are hereby corrected as shown below:

Column 2, lines 23-24  Replace "crystallization"
With --crystallized--

Column 4, line 59  Replace "morpholmes"
With --morpholines--

Column 6, lines 26-27  Replace "materials entrapped reaction solvent products of side reactions and/or"
With --materials, entrapped reaction solvent, products of side reactions, and/or--

Signed and Sealed this

First Day of May, 2001

Attest:

NICHOLAS P. GODICI

*Attesting Officer*   *Acting Director of the United States Patent and Trademark Office*